(12) United States Patent
Reiss

(10) Patent No.: US 6,418,347 B1
(45) Date of Patent: Jul. 9, 2002

(54) TRANSCUTANEOUS MEDICAL ELECTRODE FOR CONNECTING TO A TOUCH PROOF CONNECTOR

(75) Inventor: Hans William Reiss, Encinitas, CA (US)

(73) Assignee: Medserv Group, Inc., Vista, CA (US)

( * ) Notice: Subject to any disclaimer, the term of this patent is extended or adjusted under 35 U.S.C. 154(b) by 0 days.

(21) Appl. No.: 09/375,773

(22) Filed: Aug. 17, 1999

(51) Int. Cl.⁷ .............................................. A61N 1/04
(52) U.S. Cl. ....................................... 607/115; 600/384
(58) Field of Search .................................. 600/372, 373, 600/378, 382, 384, 386, 391, 392, 393, 394, 544, 545, 546; 607/46, 48, 63, 115, 116, 118, 126, 130, 142, 148, 152; 439/909

(56) References Cited

U.S. PATENT DOCUMENTS 4,632,121 A * 12/1986 Johnson et al. ............. 128/639
5,632,274 A * 5/1997 Quedens et al. ............ 128/642

* cited by examiner

*Primary Examiner*—Jeffrey R. Jastrzab
*Assistant Examiner*—Frances P. Oropeza
(74) *Attorney, Agent, or Firm*—Frank G. Morkunas

(57) ABSTRACT

A transcutaneous medical electrode for use with devices for introduce electrical signals into areas of the body or for receiving electrical signals from body areas. The electrode includes a flexible electrically conductive sheet having an electrically conductive adhesive layer on one surface. A female connector having an opening for receiving a conventional lead wire tip is secured to the opposite surface of the sheet. A sheathed male connector includes a tip for insertion into the female connector opening without exposing the tip to touching by the operator of the device or the patient. The female connector is preferably tubular with an approximately axial opening. The female connector may be secured to the sheet, parallel to the sheet, with the male connector receiving end extending beyond and edge of the sheet. Alternatively, the female connector may be secured to the sheet in a bent arrangement with the male connector receiving end extending away from the sheet at an angle and the other end bonded to the sheet.

10 Claims, 1 Drawing Sheet

TRANSCUTANEOUS MEDICAL ELECTRODE FOR CONNECTING TO A TOUCH PROOF CONNECTOR

FIELD OF THE INVENTION

This invention relates to electrodes for attachment to the skin of a patient for coupling electrical energy into nerves and muscles for stimulation thereof, for detecting electrical signals from a body indicative of physiological activity.

BACKGROUND OF THE INVENTION

A number of different medical procedures require the placement of electrodes, generally thin sheets of conductive rubber-like material having an adhesive coating, at selected positions on the skin. Lead wires connect each electrode to a central treatment or measurement device.

A major use of such electrodes is in transcutaneous electrical nerve stimulation (TENS) procedures. A high voltage electrical signal is transmitted from the electrodes through the skin to appropriate underlying nerves to help prevent pain signals from reaching the brain. The electrodes are generally disposable to prevent transferring contaminates from one patient to another.

In the past, lead wires have generally been connected to such electrodes by inserting a bare end of a lead wire into a corresponding opening in the electrode. Typical of such connection systems are those described by Mitchiner in U.S. Pat. No. 5,168,875 and Montecalvo et al. in U.S. Pat. No. 5,330,527.

The exposed lead wire tip can easily be touched by a person operating the device while inserting the tip into the electrode or during treatment if the tip is not fully inserted, possibly resulting in a shock to the operator. If the device has more than one output, with one connected to a patient, inadvertent contact by the unused leadwire to a high voltage power source could result in a shock to the patient. European statutes require use of touch proof leadwire connectors.

Others have connected instruments to electrodes by providing a short wire permanently fastened to the electrode at one end, with a connector at the other end for connection to an instrument lead wire. Typical of such arrangements is that described by Westbrook in U.S. Pat. No. 5,010,896. These arrangements are cumbersome, with both male and female connectors next to each electrode, are undesirably expensive for use with disposable electrodes and generally the lead wire end is exposed and may be touched by the operator when inserting it into the female connector or by the operator or patient during treatment if the wire end is not fully inserted.

Complex locking tips for lead wires to lock into a corresponding electrode opening have been developed, such as that described by Lyons in U.S. Pat. No. 5,465,715. These are complex and expensive for use in a disposable electrode and the lead wire tip is generally exposed and may be touched by the operator or patient during insertion or use or inadvertently inserted into a high voltage power supply.

Therefore, there is a continuing need for improved transcutaneous medical electrodes and arrangements for connecting such electrodes to device lead wires that prevent inadvertent touching of lead wire tips, that are highly efficient and easy to use and are simple and inexpensive to manufacture.

SUMMARY OF THE INVENTION

The above-noted problems, and others, are overcome in accordance with this invention by a transcutaneous medical electrode and connection system that basically comprises a flexible electrically conductive sheet having a layer of adhesive on one surface, and a female connection member secured to the opposite surface with a connection end extending away from the sheet.

The female connector has a tubular end portion out of contact with the sheet, preferably extending past one edge of the sheet or extending upwardly at an angle to the sheet. The female connector is configured to receive a typical male touch proof connector having an elongated central conductor tip and an electrically insulating sheath surrounding and spaced away from the central conductor. The female connector tubular end portion is sized to fit over the central conductor tip in a tight sliding relationship so that some force is required for removal of the central conductor. Similarly, the exterior of the tubular end portion of the female connector is configured to fit into the sheath, preferably in a tight, slidable, manner to also resist inadvertent removal.

The sheath extends far enough beyond the end of the central conductor tip to prevent any possible accidental contact between the conductor and a device operator or a patient during insertion of the male connector into the female connector or during operation of the medical device.

BRIEF DESCRIPTION OF THE DRAWING

Details of the invention and of preferred embodiments thereof will be further understood upon reference to the drawing, wherein.

DETAILED DESCRIPTION OF PREFERRED EMBODIMENTS

Figure 1:
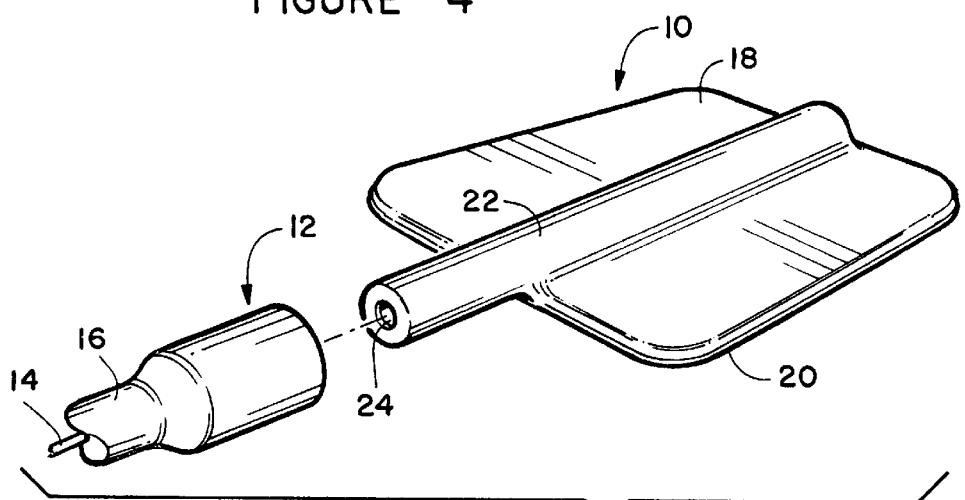
FIG. 1 is a perspective view of a first embodiment of the electrode of this invention and a typical male touch proof connector.
Figure 2:
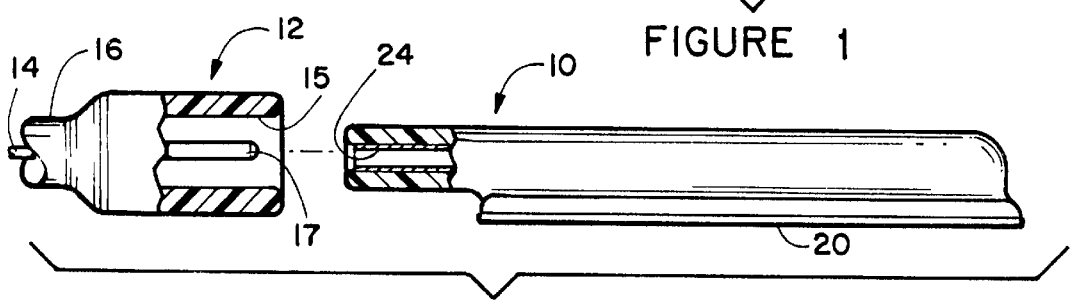
FIG. 2 is a side elevation view of the embodiment of FIG. 1 with portions of the devices cut-away.

Referring now to FIGS. 1 and 2, there is seen a transcutaneous medical electrode 10 and the end portion of a device lead wire with a typical male touch proof connector 12 having an electrically insulating outer portion.

Electrode 10 and connector 12 may connect via a conventional lead wire 14, covered with insulation 16, to any suitable machine that uses conductive electrodes bonded to a patient's skin, such as TENS and EKG devices. Lead wire 14 has a cavity 15 within which a tip 17 on lead wire 14 is exposed. Tip 17 could be the end of a single wire 14. Alternately, wire 14 could be a flexible multi-stranded wire connected to a single tip 17 within insulation 16 at the base of connector 12, or tip 17 could be a stranded wire end, tinned with solder to form a unitary tip, as desired Electrode 10 includes a sheet 18 of a flexible, electrically conductive material, such as rubber or plastic containing carbon or metal particles. For best results, a silicone sheet containing carbon particles is preferred.

A layer of adhesive 20 covering the lower surface of sheet 18 may be used to attach the electrode to the skin. Any other convention method of attaching the electrode to the skin may be used, such as adhesive tape or elastic bandaging.

A female connector 22 is secured to the surface of sheet 18. An opening 24 extending into one end of connector 22 has a diameter substantially equal to the diameter of tip 17. Ideally, opening 24 should be expanded slightly by tip 17 when inserted to allow reasonably easy insertion while providing sufficient friction to resist inadvertent removal of the tip and also to ensure adequate electrical contact between the conducting surfaces of tip 17 and opening 24. Tip 17 may extend into the female connector opening any suitable distance.

Female connector 22 has a substantially uniform cross-section, having any suitable cross-sectional configuration. A circular cross-section is preferred for ease of pushing male connector 12 over female connector 22. The end of female connector 22 has a configuration substantially matching that of cavity 15 in the male connector. Connector 22 should fit fairly tightly into cavity 15 so as to provide easy connection with sufficient friction to reduce chances of accidental removal. If the friction between tip 17 and opening 24 is sufficient to prevent accidental removal, then connector 22 may fit loosely inside cavity 15.

Connector 22 is preferably co-molded or co-extruded with sheet 18 from the same electrically conductive material. Typically, a mold or die is made corresponding to the combined connector 22 and sheet 18, then filled by injection of a suitable material into the mold or through the die. Alternatively, connector 22 could be made separately and heat bonded or adhesively bonded to sheet 18 with a conductive adhesive. Connector 22 extends beyond an edge of sheet 18 a distance sufficient to at least permit completing seating of connector 12 over connector 22, with tip 17 inserted in opening 24. The portion of connector 22 that is secured to sheet 18 may have any suitable configuration. As can be seen, the device operator and patient are protected against any accidental touching of tip 17 at any time during emplacement of electrode 10, operation of the device or removal of connector 12.

Figure 3:
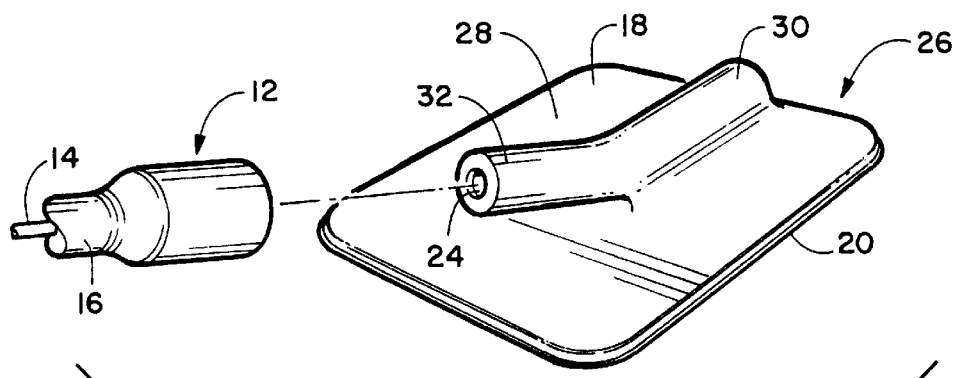
FIG. 3 is a perspective view of a second embodiment of the electrode of this invention and a typical male touch proof connector.
Figure 4:
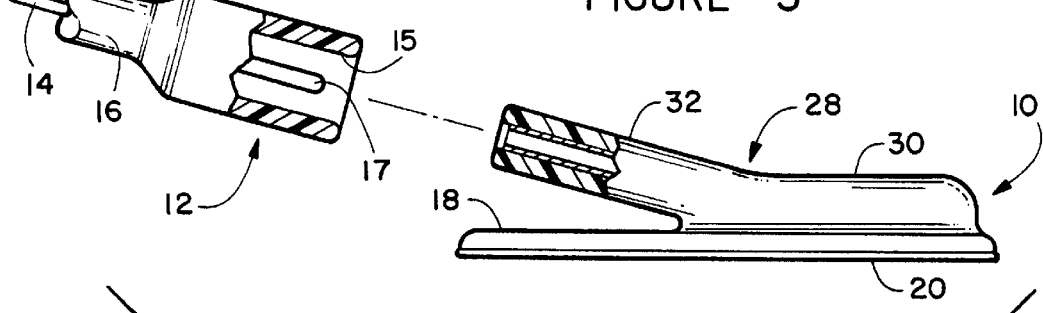
FIG. 4 is a side elevation view of the embodiment of FIG. 3 with portions of the devices cut-away.

FIGS. 3 and 4 detail an alternate embodiment of the electrode. Here, electrode 26 includes a sheet 18 of electrically conductive material with an electrically conductive adhesive layer as described above. Male connector 12 is identical with that used with the embodiment of FIGS. 1 and 2, including lead wire 14, cavity 15, insulation 16 and tip 17.

In the FIGS. 3 and 4 embodiment, female connector 28 is bent to provide a first end 30 that is secured to sheet 18. Second end 32 of connector 28 extends away from sheet 18 at a selected angle. While any suitable angle may be used, for best results the angle is from about 0 to 40 degrees to the surface of sheet 18. While second end 32 may have any suitable cross-section, the round shape shown, with an axial opening, is preferred for ease of connection.

As before, connector 32 is preferably co-molded with sheet 18 or may be bonded thereto in any suitable manner or co-extruded with a portion of connector 32 later separated from sheet 18 such as by cutting after extrusion. First end 30, which is secured to sheet 18, may have any suitable configuration. Typically, end 30 may be cylindrical as shown, flat, semi-circular with a flat side against sheet 18, etc.

The typical male touch proof connector for use with female connector 28 is the same as connector 12 discussed above. This embodiment has the advantage of easy placement on areas of the body where an adjacent body part or area might interfere with insertion in a plane parallel to sheet 18 as is done with the embodiment seen in FIGS. 1 and 2. On the other hand, the embodiment of FIGS. 1 and 2 has advantages in compact stacking and storage.

Other applications, ramifications and variations of this invention will occur to those skilled in the art upon reading the present disclosure. Those are intended to be included within the scope of this invention, as defined in the appended claims.

I claim:
1. A transcutaneous medical electrode which comprises:
   a flexible electrically conductive sheet having first and second surfaces; and
   a flexible tubular connector member on said sheet having a first end portion extending substantially apart from said sheet and further having a pin receiver at said first end portion, said tubular connector member adapted to receive a sheath of an external touch-proof connector over and around said tubular connector member and to receive a conductive pin recessed within the sheath of the external touch-proof connector into said pin receiver to thereby form a conductive connection between said electrode and the external touch-proof connector; whereby, as a user connects the external touch-proof connector to said electrode said user is prevented from contacting the external touch-proof conductive pin during the connection process of the external touch-proof connector to said tubular connector member and during use of said electrode.

2. The transcutaneous medical electrode according to claim 1 wherein said first end portion lies substantially parallel to said second surface of said sheet and extends beyond an edge of said sheet.

3. The transcutaneous medical electrode according to claim 1 wherein said first end portion lies at an angle of up to about 20° to said sheet.

4. The transcutaneous medical electrode according to claim 1 wherein said sheet and said tubular connector member comprise a single-piece molded or extruded unit.

5. The transcutaneous medical electrode according to claim 1 wherein said first end portion has a circular cross-section and an opening is along an axis of said first end portion.

6. The transcutaneous medical electrode according to claim 1 further including a layer of electrically conductive adhesive on said first surface.

7. The transcutaneous medical electrode according to claim 1 wherein the connector conductive pin has a cross sectional area slightly greater than that of said pin receiver so that insertion of the conductive pin will expand said pin receiver.

8. A transcutaneous medical electrode which comprises:
   a flexible electrically conductive sheet having first and second surfaces; and
   a flexible tubular connector member on said sheet having a first end portion extending substantially apart from said sheet and further having a pin receiver at said first end portion, said first end portion lying at an angle of up to about 20° to said sheet, said tubular connector member adapted to receive a sheath of an external touch-proof connector over and around said tubular connector member and to receive a conductive pin recessed within the sheath of the external touch-proof connector into said pin receiver to thereby form a conductive connection between said electrode and the external touch-proof connector; whereby, as a user connects the external touch-proof connector to said electrode said user is prevented from contacting the conductive pin during the connection process of the external touch-proof connector to said tubular connector member and during use of said electrode.

9. The transcutaneous medical electrode according to claim 8 wherein said sheet and said tubular connector member comprise a single-piece molded or extruded unit.

10. The transcutaneous medical electrode according to claim 8 wherein said first end portion has a circular cross-section and an opening is along an axis of said first end portion.

* * * * *